Oct. 25, 1955 H. E. HIRAOKA Plant Pat. 1,426

PEACH TREE

Filed Jan. 31, 1955

WITNESS

Addison E. Avery

INVENTOR

Harry E. Hiraoka

Webster & Webster

ATTYS.

United States Patent Office

Plant Pat. 1,426
Patented Oct. 25, 1955

1,426

PEACH TREE

Harry E. Hiraoka, Fowler, Calif.

Application January 31, 1955, Serial No. 485,359

1 Claim. (Cl. 47—62)

This discovery relates to a new and distinct variety of peach tree which bears large, yellow firm fleshed, freestone fruit having relative deep yellow skin with red markings.

The present variety of peach tree is distinctively characterized, in comparison to certain other varieties, by fruit which is larger, more uniform in size, and having deeper yellow skin with more red color than the Blazing Gold peach (United States Plant Patent No. 1127); by a ripening period which averages thirty to thirty-five days earlier than the July Elberta peach (United States Plant Patent No. 15), and one week earlier than the Gold Dust peach (United States Plant Patent No. 1144).

Further, the fruit of the present variety of peach is advantageously characterized, for market use, by reason of flesh having few fibers and ripening evenly; good shipping quality; good to best eating quality; excellent flavor, which is sweet and mild; and no split pits.

This new and distinct variety of peach tree was discovered by me in an orchard on my ranch near Fowler, Fresno County, California, growing as a bud mutation on a July Elberta peach tree. When such bud mutation came into bearing I recognized its novel features, as described above.

Having found that the variety bore fruit which had substantial commercial potential I determined to undertake propagation of the variety, and this was accomplished by me on my ranch, located as aforesaid, by budding the variety on a Lovell peach (unpatented) seedling. When such asexual reproduction grew to maturity and came into bearing it was found to carry forward all of the characteristics of the parent. Subsequent asexual reproduction of the variety likewise have run true.

Figures 1, 2:
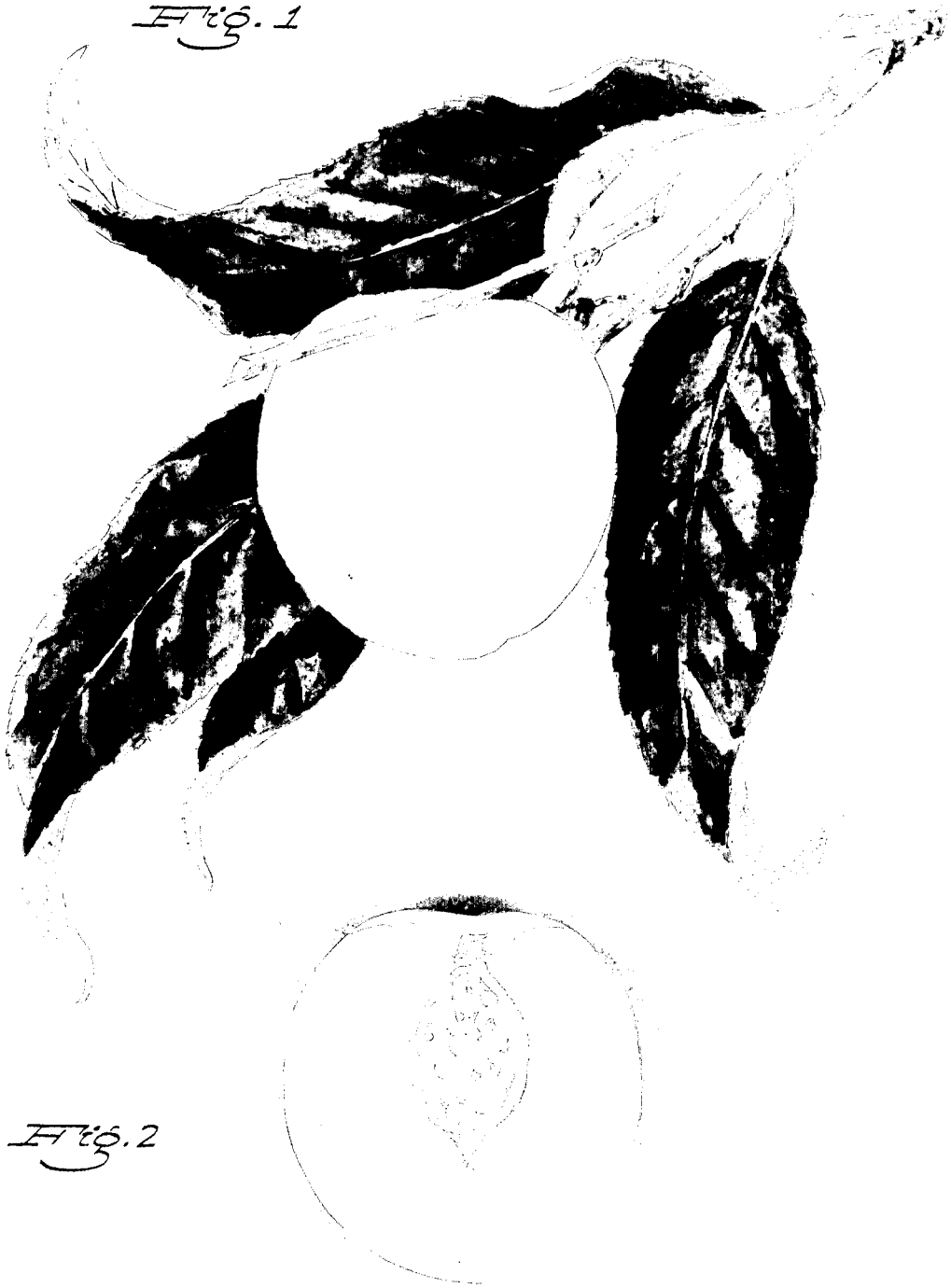
Fig. 1 is an elevation of one of the fruit, together with twigs and leaves.
Fig. 2 is a sectional elevation of one of the fruit with the stone exposed.

Referring now more specifically to the pomological details of this new and distinct variety of peach tree, the following is an outline description thereof; all major color plate identifications being by reference to Maerz and Paul Dictionary of Color.

Tree:
- *Size.*—Large.
- *Vigor.*—Vigorous.
- *Growth.*—Upright.
- *Density.*—Dense.
- *Hardiness.*—Hardy.
- *Production.*—Productive.
- *Bearing.*—Regular bearer.

Trunk:
- *Size.*—Stocky.
- *Surface.*—Medium.

Branches:
- *Size.*—Medium.
- *Surface.*—Medium.

- *Color.*—Brown.
- *Lenticels.*—Medium number; medium size.

Leaves:
- *Size.*—Large to medium; average length—6"; average width—1⅝".
- *Form.*—Oval to ovate; abruptly pointed.
- *Thickness.*—Medium.
- *Surface.*—Smooth.
- *Color.*—Top side—medium to dark green (22–L–8). Under side—lighter green (21–K–4).
- *Margin.*—Crenate.
- *Petiole.*—Medium length; medium thickness.
- *Glands.*—Average number—two. Opposite; medium size; green. Position—mostly on petiole.
- *Stipules.*—None.

Flower buds: Hardy; medium size; medium length; plump; free; pubescent.

Flowers:
- *Date of first bloom.*—On or about March 8th.
- *Date of full bloom.*—On or about March 15th. Late as compared with other varieties. Medium size. Salmon color.

Fruit:
- *Maturity when described.*—Eating ripe.
- *Date of first picking.*—June 5, 1954.
- *Date of last picking.*—June 13, 1954.
- *Size.*—Large. Average diameter axially—2¾" to 3". Average transversely in suture plane 2¾".
- *Form.*—Uniform; symmetrical; globose.
- *Suture.*—Shallow. Extends from base to beyond apex. Slight depression beyond pistil point.
- *Ventral surface.*—Rounded; strongly lipped; lips equal.
- *Cavity.*—Elongated in suture plane with suture showing on one side. Average depth—1/16"; average breadth—1/16".
- *Base.*—Rounded.
- *Apex.*—Short; depressed.
- *Pistil point.*—Lacking.

Skin:
- *Texture.*—Medium thickness; medium tender; free.
- *Down.*—Moderate.
- *Color.*—Relatively deep yellow (9–K–4, shading to 9–J–9), partly over-spread with relatively deep red (5–L–6) near base, with lighter red mottling and streaking (3–I–11) extending in the direction of the apex.

Flesh:
- *Amygdalin.*—Moderate.
- *Juice.*—Moderate.
- *Texture.*—Firm.
- *Fibers.*—Few.
- *Ripens.*—Even.
- *Flavor.*—Sweet and mild.
- *Aroma.*—Wanting.
- *Eating quality.*—Good to best.
- *Color.*—Yellow (9–K–6, shading to 9–C–9).
- *Surface of pit cavity.*—Yellow (9–K–6).

Stone:
- *Type.*—Free. Retains short fiber-like threads along ridges.
- *Size.*—Small. Average length—1¼"; average breadth—⅞"; average thickness—⅝".
- *Form.*—Oblong.
- *Base.*—Straight.
- *Hilum.*—Narrow.
- *Apex.*—Rounded.
- *Sides.*—Equal.
- *Surface.*—Regularly furrowed near base. Pitted from base to above center.
- *Ridges.*—Rounded; on either side; continuous.
- *Pits.*—Elongated.

*Ventral edge.*—Thick. Without wing toward base.
*Dorsal edge.*—Full, with shallow broad groove throughout.
*Tendency to split.*—None.
*Color.*—Tan (11–H–6, shading to 11–H–8).
Use: Market; local, and long distance shipping.
Keeping quality: Good.
Shipping quality: Good.

The tree and its fruit herein described may vary in slight detail due to climatic and soil conditions under which the variety may be grown.

The following is claimed:

A new and distinct variety of peach tree, substantially as illustrated and described, which bears large, yellow and firm fleshed, evenly ripening, freestone fruit having relatively deep yellow skin over-spread in part with deep red near the base with lighter red mottling and streaks extending toward the apex; the fruit—in comparison to the Blazing Gold peach—being larger and more uniform in size, and having deeper yellow skin with more red thereon; in comparison to the July Elberta peach—by ripening thirty to thirty-five days earlier; and—in comparison to the Gold Dust peach—by ripening approximately one week earlier; and being additionally characterized by fruit which has few fibers, good shipping quality, good to best eating quality, excellent flavor which is sweet and mild, and no split pits.

No references cited.